United States Patent [19]

Erpenbach et al.

[11] Patent Number: 4,549,937
[45] Date of Patent: Oct. 29, 1985

[54] PROCESS FOR SEPARATING THE CATALYST SYSTEM FROM THE REACTION MIXTURES OF CARBONYLATION REACTIONS

[75] Inventors: Heinz Erpenbach, Cologne; Klaus Gehrmann; Peter Hörstermann, both of Erftstadt; Hans-Klaus Kübbeler, Swisttal; Georg Kohl, Hürth, all of Fed. Rep. of Germany

[73] Assignee: Hoechst Aktiengesellschaft, Fed. Rep. of Germany

[21] Appl. No.: 442,107

[22] Filed: Nov. 16, 1982

[30] Foreign Application Priority Data

Dec. 11, 1981 [DE] Fed. Rep. of Germany ....... 3149092

[51] Int. Cl.[4] .................. B01D 3/06; C07C 51/56
[52] U.S. Cl. .................................. 203/40; 203/73; 203/74; 203/77; 203/80; 203/81; 203/88; 560/232
[58] Field of Search ............. 203/40, 50, 51, 71, 203/73, 74, 77, 81, 88, 91, 70, 80, 49; 562/519; 560/232; 568/411, 387; 202/197

[56] References Cited

U.S. PATENT DOCUMENTS

| | | | |
|---|---|---|---|
| 3,845,121 | 10/1974 | Eubanks et al. ............... | 562/519 |
| 4,252,741 | 2/1981 | Porcelli et al. ............... | 560/232 |
| 4,381,221 | 4/1983 | Isshiki et al. ............... | 562/519 |
| 4,409,064 | 10/1983 | Vora et al. ............... | 203/40 |
| 4,412,887 | 11/1983 | Dye ............... | 203/40 |
| 4,433,166 | 2/1984 | Singleton et al. ............... | 562/519 |

Primary Examiner—S. Leon Bashore
Assistant Examiner—Virginia Manoharan
Attorney, Agent, or Firm—Connolly and Hutz

[57] ABSTRACT

The disclosure relates to a process for separating the catalyst system from reaction mixtures which are obtained by reacting methyl acetate and/or dimethylether with carbon monoxide and optionally hydrogen at elevated temperatures to acetic anhydride and optionally ethylidene diacetate in the presence of a catalyst system consisting of carbonyl complexes of noble metals belonging to group VIII of the Periodic System, acetic acid, an organophosphorus or organonitrogen compound, methyl iodide and optionally compounds of carbonyl-yielding common metals, and which issue from the reaction zone under a pressure of 25 to 150 bars at a temperature of 100° to 250° C. More particularly, the reaction mixture coming from the reaction zone is introduced into a separator heated to 60° to 140° C. and released to a pressure of 0.5 to 3.5 bars with spontaneous evaporation of the bulk of volatile constituents; the stream of liquid matter coming from the separator is delivered to a distilling zone and the bulk of still volatile constituents is distilled off therein under a pressure of 0.05 to 1 bar at a base temperature of 70° to 170° C.; and catalyst solution retained as base product is recycled to the reaction zone.

4 Claims, 1 Drawing Figure

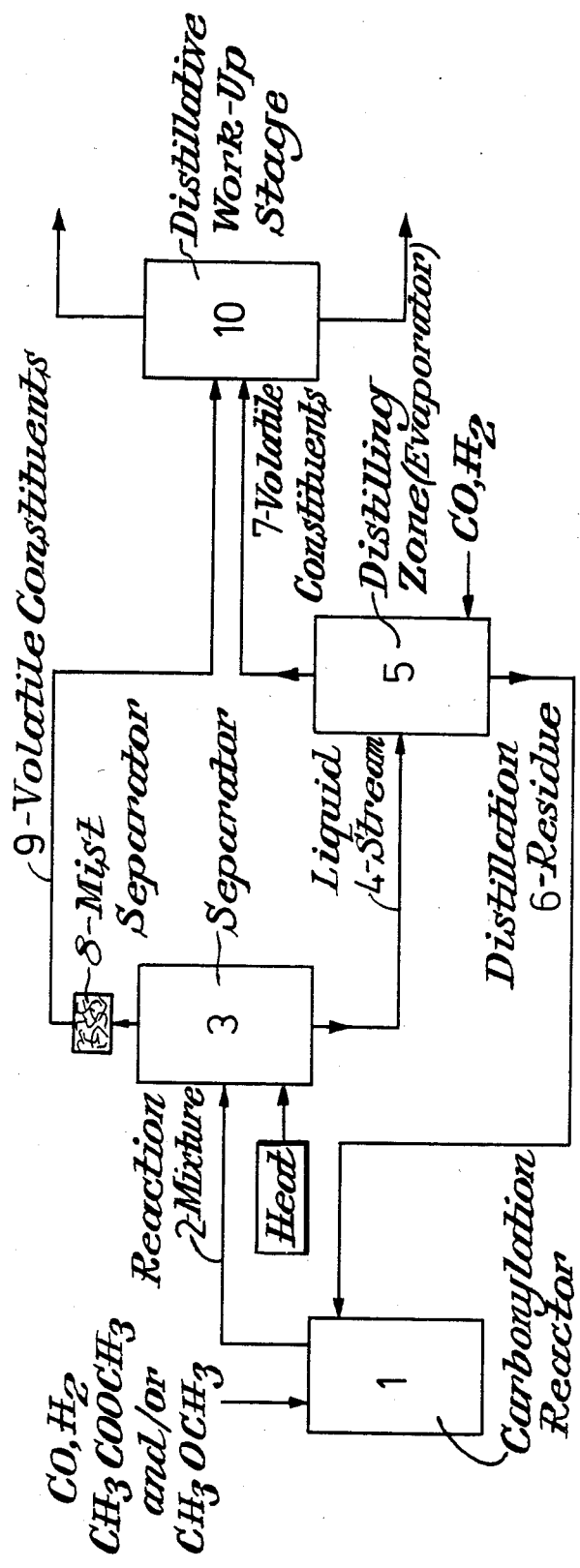

PROCESS FOR SEPARATING THE CATALYST SYSTEM FROM THE REACTION MIXTURES OF CARBONYLATION REACTIONS

The present invention relates to a process for separating the catalyst system from reaction mixtures which are obtained by reacting methyl acetate and/or dimethylether with carbon monoxide and optionally hydrogen at elevated temperatures to acetic anhydride and optionally ethylidene diacetate in the presence of a catalyst system consisting of carbonyl complexes of noble metals belonging to group VIII of the Periodic System, acetic acid, an organophosphorus or organonitrogen compound, methyl iodide and optionally compounds of carbonyl-yielding common metals, such as disclosed in DE-A- Nos. 2450965, 2836084, 2939839 and 2941232, and which issue from the reaction zone under a pressure of 25 to 150 bars and at a temperature of 100° to 250° C.

A process for separating the catalyst from such reaction mixtures has already been disclosed in DE-A- No. 2940752. As disclosed therein, the reaction mixture is distillatively separated into volatile products and catalyst system inside a flash distilling chamber under a pressure of 3.8 to 5.2 bars and at temperatures of 110° to 130° C. in the presence of a hydrogen partial pressure of at least 0.7 bar and carbon monoxide partial pressure of at least 1 bar.

A similar separating process, wherein the reaction product is distilled under a pressure of 0.5 to 1 bar in the presence of a carbon monoxide partial pressure of at least 0.01 bar and separated into volatile constituents and catalyst system has been described in DE-A- No. 3013257.

A still further process wherein the product mixture under pressure is treated in a separating zone without supply of heat and released to a pressure of at least 0.14 bar lower than reaction pressure, preferably atmospheric pressure, the carbonylation products are partially evaporated and remaining reaction mixture is recycled to the reactor, has been described in DE-A- No. 2211203.

These processes are based on the experience that it is necessary for the thermal stress the reaction mixture is subjected to during the distillative separation of volatile carbonylation products from the catalyst system to be kept as small as possible in the interest of an unimpaired catalyst activity. This is the reason why the volatile constituents are evaporated by adiabatic release without supply of heat in DE-A No. 2211203. This is readily possible in the production of acetic acid as described therein. In the event of a reaction mixture containing important proportions of compounds with a boiling point higher than that of acetic acid, such as acetic anhydride or ethylidene diacetate, the process just referred to fails to work as the heat enthalpy of the reaction mixture is insufficient for effecting the evaporation of the reaction products. In other words, it is indispensable for heat to be supplied from the outside to effect the distillative separation of volatile constituents. The adverse effect of the high distillation temperatures can be acted upon by effecting the separation in the presence of carbon monoxide and optionally hydrogen as described in DE-A- Nos. 2940752 and 3013257. In these two latter processes, the work up stage is operated under a pressure of 0.5 to 5.2 bars and the entire stream of products coming from the reactor is directly introduced into an evaporator whereby the catalyst is naturally subjected to heavy thermal stress.

It is therefore the target of the present invention to free the reaction mixtures of carbonylation reactions as described hereinabove from the catalyst under conditions preventing it from becoming decomposed or inactivated so that it can be recycled to the reactor without loss which would be caused by reactivation.

To achieve this, the invention provides for the reaction mixture coming from the reaction zone to be introduced into a separator heated to 60° to 140° C. and to be released to a pressure of 0.5 to 3.5 bars with spontaneous evaporation of the bulk of volatile constituents; for the stream of liquid matter coming from the separator to be delivered to a distilling zone and for the bulk of still volatile constituents to be distilled off under a pressure of 0.05 to 1 bar at a base temperature of 70° to 170° C.; and for the catalyst solution retained as base product to be recycled to the reaction zone.

Further preferred and optional features of the present process provide;
(a) for the distillative separation in the distilling zone to be effected in the presence of carbon monoxide and optionally hydrogen;
(b) for the volatile constituents separated in the separator and distilling zone, respectively, to be combined and jointly worked up distillatively;
(c) for the volatile constituents evaporated in the heated separator to be passed through a mist separator preventing liquid droplets from being carried along; and
(d) for the mist separator to have filter gauze of corrosionproof materials, preferably glass fibers or stainless steel, placed therein.

The reaction mixture issuing from the reaction zone under a pressure of 25 to 150 bars should preferably have a temperature of 150° to 200° C. and should preferably be released in a separator heated to 70° to 130° C. to a preferred pressure of 0.8 to 2 bars, the bulk of unreacted feed materials and final products undergoing spontaneous evaporation.

In this manner, it is possible for a good deal of the volatile reaction products to be separated from the dissolved catalyst system, under mild conditions. Next, the stream of liquid matter retained is freed by short path distillation under a pressure of 0.05 to 1 bar, preferably in the presence of carbon monoxide and optionally hydrogen, from the bulk of volatile reaction products still contained therein, the catalyst solution remaining behind as base material being recycled to the reactor. The vapor mixture separated in the separator and head product coming from the short path distillation zone are jointly subjected to work-up. As a result of the advance separation of the product portions evaporating in the separator, no more than 10 to 40 weight% of the overall quantity of constituents to be evaporated have to be separated in the successive distilling zone whereby the thermal stress the catalyst is subjected to becomes minimized.

The invention will now be described with reference to the accompanying drawing:

Reaction mixture obtained by carbonylation is taken from carbonylation reactor 1 and introduced through line 2 into separator 3. The stream of products consisting of dissolved gas and liquid coming from the reactor is under a pressure of 25 to 150 bars and has a temperature of 100° to 250° C., preferably 150° to 200° C.

In separator 3 heated to 70° to 130° C., the product stream is released to a pressure of 0.5 to 3.5 bars, preferably 0.8 to 2 bars, and separated into a liquid matter portion and vaporous matter portion, respectively. The liquid matter portion is introduced through line 4 into evaporator 5 which is optionally provided with five series-connected distilling trays. The evaporator may be formed of a circulation evaporator permitting the thermal stress the catalyst is subjected to to be reduced; it is more preferable however to use a falling stream or thin layer evaporator. The evaporator should be operated either at atmospheric pressure (1013 millibars) at a base temperature of 134° C. or alternatively under reduced pressure at a correspondingly lower temperature, e.g. at 150 millibars at 96° C. In order to avoid adverse affects on the catalytic activity, it is good practice to introduce, per hour, 1 to 100 liters, preferably 10 to 25 liters, carbon monoxide or optionally a mixture of carbon monoxide and hydrogen into the base portion of evaporator 5. The liquid distillation residue which has the catalyst system dissolved therein, is repumped through line 6 to reactor 1. The volatile constituents coming from evaporator 5, consist substantially of acetic anhydride and acetic acid together with ethylidene diacetate, methyl iodide and unreacted methyl acetate; they flow through line 7 and are introduced jointly with vaporous matter coming from separator 3 through mist separator 8 and line 9 into the distillative work-up stage 10 which does not form part of the invention, the mist separator 8 being packed with filter gauze of glass fibers or Hastelloy B.

EXAMPLE 1

5841 g/h reaction product was taken from carbonylation reactor 1 under a pressure of 75 bars and at a temperature of 180° C., and introduced into separator 3. In separator 3 maintained under a pressure of 1.1 bars and at a wall temperature of 75° C., 2829 g/h vaporous constituents (67 weight% of total products evaporated) were separated from the liquid constituents, the vaporous constituents consisting of 25.14 weight% acetic anhydride, 11.35 wgt% acetic acid, 0.24 wgt% ethylidene diacetate, 37.63 wgt% methyl acetate, 22.99 wgt% methyl iodide, 0.42 wgt% acetone, 1.8 wgt% carbon monoxide, 0.13 wgt% carbon dioxide, 0.03 wgt% methane and 0.27 wgt% nitrogen. The vaporous constituents were introduced through mist separator 8 into the first separating stage of the work-up stage 10 which does not form part of the invention. The liquid constituents, 3012 g/h, were introduced into a falling stream evaporator 5 provided with five series-connected distilling trays, in which volatile constituents were separated at 1 bar at a base temperature of 134° C., the base portion of the evaporator being fed per hour with 16 liters synthesis gas (CO: $H_2$=1:1). 1388 g/h volatile constituents (33 wgt% of the total products evaporated) which were composed of 57.2 wgt% acetic anhydride, 22.6 wgt% acetic acid, 16.7 wgt% methyl acetate and 3.5 wgt% methyl iodide were equally introduced into the first separating stage of distillative work-up stage 10. 1624 g/h catalyst solution which contained 23.4 wgt% acetic anhydride, 6.15 wgt% acetic acid, 0.38 wgt% ethylidene diacetate and 70.07 wgt% catalyst system (Rh-complex and methyltributylphosphonium iodide) was obtained as base product in evaporator 5. It was recycled to reactor 1.

EXAMPLE 2

23 450 g/h reaction product was taken from carbonylation reactor 1 under a pressure of 70 bars at 184° C. and introduced into separator 3. In separator 3 maintained under a pressure of 1.4 bars and at a wall temperature of 125° C., 14,750 g/h vaporous constituents (89 wgt% of the total products evaporated) were separated from the liquid constituents, the vaporous constituents consisting of 19.42 wgt% acetic anhydride, 13.6 wgt% acetic acid, 0.11 wgt% ethylidene diacetate, 42.51 wgt% methyl acetate, 23.32 wgt% methyl icdide, 0.56 wgt% acetone, 0.47 wgt% carbon monoxide, 0.02 wgt% carbon dioxide, 0.01 wgt% methane and 0.09 wgt% nitrogen. The liquid constituents (8700 g/h) were introduced into a falling stream evaporator 5 with five distilling trays, in which the volatile constituents were separated under a pressure of 150 millibars and at a base temperature of 96° C., the base portion of the evaporator being fed per hour with 18 liters synthesis gas (CO: $H_2$=1:1). 1800 g/h volatile constituents (11 wgt% of the total products evaporated) composed of 36 wgt% acetic anhydride, 35 wgt% acetic acid, 22.8 wgt% methyl acetate and 6.2 wgt% methyl iodide was obtained. The distillate and vaporous constituents taken from separator 3 through mist separator 8 were introduced jointly into first stage of work-up stage 10 which does not form part of the invention. 6900 g/h catalyst solution which contained 18 wgt% acetic anhydride, 11.68 wgt% acetic acid, 0.12 wgt% ethylidene diacetate and 70.2 wgt% catalyst system (Rh-complex and methyltributylphosphonium iodide) was obtained as base product in evaporator 5; it was recycled to the reactor 1.

EXAMPLE 3

4676 g/h reaction product was taken from carbonylation reactor 1 under a pressure of 90 bars at 186° C. and introduced into separator 3. In separator 3 maintained under a pressure of 0.9 bar and at a wall temperature of 110° C., 2212 g/h vaporous constituents (68 wgt% of the total products evaporated) were separated from the liquid constituents, the vaporous constituents consisting of 22.24 wgt% acetic anhydride, 12.52 wgt% acetic acid, 5.83 wgt% ethylidene diacetate, 36.12 wgt% methyl acetate, 22.06 wgt% methyl iodide, 0.61 wgt% carbon monoxide, 0.49 wgt% methane and 0.13 wgt% hydrogen. The liquid constituents (2464 g/h) were introduced into a thin layer evaporator 5 with no additional distilling trays, in which volatile constituents were separated under a pressure of 100 millibars and at a base temperature of 85° C., the base portion of the evaporator being fed per hour with 16 liters carbon monoxide. 1055 g/h volatile constituents (32 wgt% of the total products evaporated) composed of 26.45 wgt% acetic anhydride, 47.78 wgt% acetic acid, 12.23 wgt% ethylidene diacetate, 9 wgt% methyl acetate and 4.55 wgt% methyl iodide, and the mixture of vaporous constituents taken from separator 3 via mist separator 8 were jointly introduced into the work-up stage 10 which does not form part of the invention. 1049 g/h catalyst solution which contained 20.23 wgt% acetic anhydride, 13.84 wgt% ethylidene diacetate, 5.32 wgt% acetic acid, and 60.61 wgt% catalyst system (Rh-complex and methyltributylphosphonium iodide) was obtained as the base product of evaporator 5; it was recycled to reactor 1.

Even after operation periods of more than 6 months, the activity of the catalyst could not be found to have been impaired in any of the above Examples.

We claim:

1. A process for separating a catalyst system from a reaction mixture obtained by reacting methyl acetate or dimethylether or a mixture thereof with carbon monoxide or a mixture of carbon monoxide and hydrogen at elevated temperatures to acetic anhydride in the presence of the catalyst system, said catalyst system comprising carbonyl complexes of noble metals belonging to Group VIII of the Periodic System, acetic acid, methyl iodide and an organophosphorus or organonitrogen compound, and said reaction mixture issuing from a reaction zone under a pressure of 25 to 150 bars at a temperature of 100° to 250° C., which comprises:

heating a separator to 60° to 140° C., introducing the reaction mixture coming from the reaction zone into said separator and releasing the reaction mixture to a pressure of 0.5 to 3.5 bars with spontaneous evaporation of the volatile constituents of said reaction mixture; delivering a stream of liquid matter coming from the separator to a distilling zone and distilling off volatile constituents still contained therein under a pressure of 0.05 to 1 bar at a base temperature of 70° to 170° C.; and recycling the catalyst system retained as base product to the reaction zone.

2. A process as claimed in claim 1, wherein the separation in the distilling zone is effected in the presence of carbon monoxide or mixtures of carbon monoxide and hydrogen.

3. A process as claimed in claim 1, wherein the volatile constituents separated in the separator and distilling zone, respectively, are combined and distilled.

4. A process as claimed in claim 1, wherein the volatile constituents evaporated in the heated separator are passed through a mist separator preventing liquid droplets from being carried along.

* * * * *